(12) United States Patent
Waanders et al.

(10) Patent No.: US 10,031,106 B2
(45) Date of Patent: Jul. 24, 2018

(54) METHOD AND APPARATUS FOR MEASURING AN AMOUNT OF SUPERPARAMAGNETIC MATERIAL IN AN OBJECT

(71) Applicant: UNIVERSITEIT TWENTE, Enschede (NL)

(72) Inventors: Sebastiaan Waanders, Enschede (NL); Martijn Visscher, Enschede (NL); Tasio Olmo Borendissi Oderkerk, Enschede (NL); Hendrikus Johannes Gradus Krooshoop, Enschede (NL); Bernard Haken, Enschede (NL)

(73) Assignee: UNIVERSITEIT TWENTE, Enschede (NL)

( * ) Notice: Subject to any disclaimer, the term of this patent is extended or adjusted under 35 U.S.C. 154(b) by 494 days.

(21) Appl. No.: 14/646,816

(22) PCT Filed: Nov. 19, 2013

(86) PCT No.: PCT/NL2013/050832
§ 371 (c)(1),
(2) Date: May 22, 2015

(87) PCT Pub. No.: WO2014/081290
PCT Pub. Date: May 30, 2014

(65) Prior Publication Data
US 2015/0338376 A1    Nov. 26, 2015

(30) Foreign Application Priority Data

Nov. 23, 2012 (EP) ..................... 12194029

(51) Int. Cl.
*G01N 27/72* (2006.01)
*G01R 33/16* (2006.01)
(Continued)

(52) U.S. Cl.
CPC .......... *G01N 27/72* (2013.01); *G01R 33/0017* (2013.01); *G01R 33/16* (2013.01); *G01N 27/76* (2013.01)

(58) Field of Classification Search
None
See application file for complete search history.

(56) References Cited

U.S. PATENT DOCUMENTS

| | | | |
|---|---|---|---|
| 8,034,634 B2 * | 10/2011 | Hong | ..................... G01N 27/74 436/518 |
| 2013/0149539 A1 * | 6/2013 | Krishnan | ........... A61K 41/0052 428/407 |
| 2014/0066751 A1 * | 3/2014 | Weiss | ................... A61B 5/0515 600/420 |

FOREIGN PATENT DOCUMENTS

| WO | 03/019188 | 3/2003 |
| WO | 2006/117530 | 11/2006 |

OTHER PUBLICATIONS

International Search Report dated Jan. 31, 2014, corresponding to PCT/NL2013/050832.
(Continued)

*Primary Examiner* — John Kuan
(74) *Attorney, Agent, or Firm* — Young & Thompson

(57) ABSTRACT

Method and apparatus for measuring an amount of superparamagnetic material in an object, the method including a) applying a magnetic field having a first component alternating with a first period to the object and a magnetic field strength lower than a magnetic field strength at which the superparamagnetic material is driven in saturation; b) measuring a first magnetic susceptibility of the object with a detection coil; c) applying a static second component to the magnetic field for a second period being equal or larger than the first period, the strength of the magnetic field during the second period is such that the superparamagnetic material is (Continued)

driven towards saturation; d) measuring a second magnetic susceptibility of the object with the detection coil during the application of the static second component; and e) determining the amount of superparamagnetic material from a difference between the measured first and second susceptibility of the object.

17 Claims, 4 Drawing Sheets

(51) Int. Cl.
  *G01R 33/00*    (2006.01)
  *G01N 27/76*    (2006.01)

(56) References Cited

OTHER PUBLICATIONS

Ludwig, et al.; "Determination of Core and Hydrodynamic Size Distributions of CoFe2O4 Nanoparticle Suspensions Using ac Susceptibility Measurements"; Journal of Applied Physics; vol. 108, No. 3; Aug. 12, 2010; pp. 33918-33918.

Oldenburg, et al.; "Imaging and Elastometry of Blood Clots Using Magnetomotive Optical Coherence Tomography and Labeled Platelets"; vol. 18, No. 3; May 1, 2012.

* cited by examiner

METHOD AND APPARATUS FOR MEASURING AN AMOUNT OF SUPERPARAMAGNETIC MATERIAL IN AN OBJECT

The invention relates to a method and apparatus for measuring an amount of superparamagnetic material in an object. The method can be used for diagnosis in oncology. Cancer staging of, for example, mamma carcinoma can be done by performing a conventional lymph node method.

In the conventional method first lymph nodes draining tumors are sought, and if these lymph nodes are found to contain metastases, this indicates a stage of the cancer spreading. A therapy can be adjusted to the outcome of this method.

Presently, this method can be performed using a radioactive contrast material or tracer and a gamma probe which detects the emanating radiation from the contrast material or tracer. This method may pose health issues for a patient and medical personnel. In a medium-sized hospital personnel perform this method about 300 times a year. Additionally, the radioactive sentinel lymph node method imposes a logistical burden onto the hospital and special measures are required for safe handling of radioactive materials. A disadvantage of this method is that many hospitals don't have the required measures in place and are thus not able to perform the sentinel lymph node method.

An alternative approach to this sentinel lymph method is an, also known, method similar to the lymph node method described above wherein the radioactive material is replaced by a magnetic tracer material comprising, for example, a suspension of superparamagnetic iron-oxide nanoparticles and the superparamagnetic iron-oxide nanoparticles can then be detected by an apparatus which is arranged to measure a susceptibility of the superparamagnetic iron-oxide nanoparticles by Faraday induction. Such an apparatus can be obtained from Endomagnetics.

Such an apparatus is known from, for example, WO2006/117530 disclosing an apparatus for determining magnetic properties of materials comprising a portable probe, an equipment trolley holding cryogenics and electronics and connecting cables. The probe comprises a drive coil and a correction coil, the drive coil being disposed symmetrically with respect to an inner second-order gradiometer sensor coil. Electrical connectors in the form of 2-meter long Belden microphone cables are used to connect the apparatus on the equipment trolley to the drive coil, the correction coil and the sensor coil. The drive coil is driven so as to generate a sinusoidally varying magnetic field. The electronics comprise a flux-locked loop, a SQUID controller, a data acquisition module, which captures and processes the signals and a computer.; A liquid-nitrogen Dewar is supported on the equipment trolley and houses a sensitive SQUID detector and a transfer coil made from copper. Possible applications of the apparatus include an intra-operative tool for sentinel lymph node detection in the treatment of breast cancer, and a non-destructive evaluation tool for detecting voids and defects in aluminum and applications in the aeronautics industry.

A drawback of the known apparatus is that this apparatus measures, besides a susceptibility of the superparamagnetic iron-oxide nanoparticles, also an unwanted contribution from the patient and the surroundings.

The article "Determination of core and hydrodynamic size distributions off CoFe2O4 nanoparticle suspensions using ac susceptibility measurements" by F. Ludwig et al, published in Journal of Applied Physics, American Institute of Physics, New York, US, vol. 108, no. 3, 12 Aug. 2010 discloses measurement of the complex susceptibility on $CoFe_2O_4$ nanoparticle suspensions in the frequency range between 1 kHz and 1 MHz for different values of a superimposed static magnetic field, wherein the frequency is sweeped from low to high frequencies. The maximum in the imaginary part $\chi''$ of the ac susceptibility shifts to higher frequencies with increasing static magnetic field. The shift is theoretically modeled utilizing the magnetic field dependence of the Brownian relaxation time constant and assuming a distribution of hydrodynamic particle sizes. The mean hydrodynamic size as determined from the maximum $\chi''$ in zero field and the mean core size as obtained from the shift of the $\chi''$ peak with static field agree very well with the data from transmission electron microscopy and dynamic light scattering measurements, respectively. The results indicate that both core and hydrodynamic size distributions can be determined from measurements on nanoparticle suspensions proposed that magnetic dipole-dipole interactions are negligible.

It is an object of the invention to provide a method and apparatus to improve the measurement of an amount of superparamagnetic material in an object.

According to a first aspect of the invention this object is achieved by a method for measuring an amount of superparamagnetic material in an object comprising:
 a) applying a first magnetic field comprising a first component alternating with a first period and a single frequency to the object and having a magnetic field strength lower than a magnetic field strength at which the superparamagnetic material is driven in saturation;
 b) measuring a first magnetic susceptibility of the object with a detection coil;
 c) applying a static second component to the magnetic field for a second period being equal or larger than the first period, the strength of the magnetic field during the second period is such that the superparamagnetic material is driven towards saturation;
 d) measuring a second susceptibility of the object with the detection coil during the application of the static second component of the magnetic field; and
 e) determining the amount of superparamagnetic material from a difference between the measured first and second susceptibility of the object.

The invention is based on the insight that a non-linear magnetization characteristics of superparamagnetic material, for example, superparamagnetic iron oxide nanoparticles or SPIONs can be exploited to distinguish in a measurement of the susceptibility of these nanoparticles from a contribution of the susceptibility of the patient and/or the surroundings, because this contribution on the susceptibility of the patient and the surrounding exhibit a linear characteristic.

In a low magnetic field, for example, lower than 1 T diamagnetic and paramagnetic contributions from the body and the environment are linear with respect to their response to an applied magnetic field in a way that the magnetization increases proportionally with an applied magnetic field. The SPIONs saturate at a certain strength of the applied magnetic field, which results in that the magnetic susceptibility of the SPION reduces to nearly zero.

According to the method of the invention in a first step the magnetic field comprising the first alternating component is applied to the object, for example, a sample comprising an amount of superparamagnetic iron oxide or a part of the body of a patient, in which a tracer of superparamagnetic iron oxide is introduced. A single frequency alternating first component of the magnetic field enables susceptometry. In a next step the magnetic susceptibility is measured with the detection coil, a signal induced in the detection coil is then modulated by the magnetization M of the sample. The signal in the detection coil is then given by $$\varepsilon = -\frac{d}{dt}\int B dA \qquad (1)$$

Where $\varepsilon$ represents the electromotive force,
$B=\mu_0(M+H)$, wherein
B represents a magnetic field,
$\mu_0$ represents the magnetic permeability of vacuum;
M represents the magnetization, and
A is the surface of the coil The detection coil can be used to measure the derivative of the magnetization curve or the magnetic susceptibility $\chi$. Now, for linear magnetic materials comprising dia- or paramagnetic material, the relation between the applied magnetic field and the magnetization is given by $$B=\chi M \qquad (2)$$

Wherein B represent the magnetic field,
$\chi$ represents the susceptibility, and
M represents the magnetization.

The induced voltage in the detection coil is dependent on the susceptibility $\chi_0$ In a further step of the method a static second component is also applied to the magnetic field applied to the sample or patient. The strength of the total magnetic field is such that the SPIONs are driven towards saturation.

In a next step the magnetic susceptibility is again measured with the detection coil during the application of the static second component. The induced voltage in the detection coil is now dependent on the susceptibility $\chi_1$. However, the value $\chi_1$ of the susceptibility measured during the application of the second magnetic field is now different from the value $\chi_0$ of the susceptibility measured without the application of the static magnetic field.

The magnetization of the SPION material is strongly nonlinear owing to the superparamagnetic properties and is commonly modeled using the Langevin equation $$M=M_s L(x) \qquad (3)$$

Where $$L = \coth x - \frac{1}{x} \text{ and } x = \frac{m_0 \mu_0 H}{k_b T} \qquad (4)$$

Wherein $M_s$ represents the saturation magnetization and L (x) represents the Langevin function,
x represents the dimensionless scaled magnetic field
$m_0$ represents the magnetic moment of a single nanoparticle
$\mu_0$ represents the magnetic permeability of vacuum,
$k_b$ represents Boltzmann's constant
T represent the temperature, and
H a magnetic field.

In this way differential susceptibility can be enabled and an amount of SPIONs can then be determined from the difference between the values $\chi_1$ and $\chi_0$.

In this way it is possible to detect an amount of SPIONs in an range between, for example, 0.5 µg and 1000 µg. Theoretically, it can be possible to detect a minimal amount as low as 1 nanogram.

An advantage of this method with respect to the conventional method using the radioactive tracer and the gamma probe is that the method according to the invention enables a cheaper and safer procedure because of a lower logistical burden on the hospital and a lower burden on the patient.

A further advantage to the known method of measuring susceptibility is that the method according to the invention enables a measurement with a reduced sensitivity for linear materials like body tissue, fat and water.

In a further embodiment of the invention the method comprises repeating steps b) to d) with a third period, wherein the third period is equal to or larger than the second period. By repeating the measurements statistics can be applied to improve the accuracy of the measured first and second values. The first period can be, for example, 0.1 ms, the second period can be 25 ms and the third period can be, for example, 50 ms.

In a further embodiment of the method in step c) a direction of the applied static component of the magnetic field in a further third period after a preceding third period is reversed with respect to the direction of the applied second magnetic field in the preceding third period. By reversing the direction of the static second component in the applied magnetic field every second period, magnetic remanence in the material is avoided. Furthermore, in this way a phase sensitivity detection method can be used. Phase sensitive detection enables isolation of a signal with a specific frequency from background noise. A further advantage is that influences due to eddy-currents in other conducting components of the apparatus can be reduced.

In a further embodiment of the method the superparamagnetic material comprises superparamagnetic iron oxide (SPIO). Superparamagnetic material for introduction in a human body is, for example, Endorem, as is available from Guerbet and comprises an aqueous colloid of superparamagnetic iron oxide coated with carboxydextran. Another example Resovist as is available from Bayer Schering Pharma AG.

According to a second aspect of the invention this object is achieved by an apparatus for measuring an amount of superparamagnetic material in an object, comprising:
means for applying a magnetic field with a first and a second component to the object;
a sensing device arranged to measure a magnetization of the object
a control device arranged to control the first component and second component of the magnetic field and the sensing device, wherein the control device is arranged to perform the method according to any of the claims 1-4.

In an embodiment of the apparatus according to the invention the means for applying a magnetic field comprising the first component and the second component can respectively comprise a first amplifier and a first coil for generating the first component and a second amplifier and a second coil for generating the second component. The first amplifier can be driven by a sine wave with the first period. For example with a period of 0.1 ms or a frequency of 10 kHz. The second amplifier can be driven, by for example, a block wave signal with a third period of twice the second period. The frequency of the block wave can be, for example, 20 Hz.

In a further embodiment of the apparatus according to the invention the first coil can be axially arranged with respect to the second coil.

In a further embodiment of the apparatus according to the invention the sensing device comprises a detection coil. A coil can be advantageously applied for measuring differences in magnetization as a function of time because the changing flux induces a voltage in the detection coil.

In a further embodiment, the detection coil is coaxially arranged within the first coil. The detection coil can be positioned close to the object to increase an induced voltage in the detection coil. It is also possible to position the detection coil opposite to the first coil.

In a further embodiment of the apparatus according to the invention the sensing device comprises a compensation coil arranged to have a mutual inductance with the first coil which is opposite to a mutual induction of the detection coil with the first coil. In this arrangement the detection coil and the compensation coil can be balanced in operation an influence of the alternating first magnetic field on the sum of an induced voltage in respectively the detection coil and the compensation coil is nil, when the detection coil and the compensation coil are geometrically balanced and no object is near the apparatus or detection coil. In case an object is placed in the holder this will introduce an asymmetry between the voltage induced in the detection coil and the compensation coil.

In a further embodiment the compensation coil is coaxially arranged within the first coil.

In a further embodiment of the apparatus according to the invention the first coil comprises a first sub-coil and a second sub-coil, wherein the first sub-coil is positioned with respect to one side of the second coil and the second sub-coil is positioned with respect to the other side of the second coil. This arrangement enables an more uniform alternating first magnetic field.

In a further embodiment of the apparatus according to the invention the detection coil is coaxially arranged with the first sub-coil and the compensation coil is coaxially arranged with the second sub-coil. In this arrangement the balancing of the detection coil and the compensation coils can be improved.

In a further embodiment of the apparatus according to the invention the sensing device comprises a third amplifier connected to a series circuit of the detection coil and the compensation coil, wherein the control device is further arranged to control the third amplifier to provide a compensation current to the detection coil and the compensation coil. This compensation current through the detection coil and the compensation coil creates an induced correction signal that compensate unwanted influence from the first coil on the detection system. This compensation enable measurement of a detection signal of about 10 µV with an AC voltage simultaneously measured with the detection signal of about 1 mV. This arrangement also reduces the maximum amplitude of the signal to be detected by the detection coil.

In a further embodiment of the apparatus according to the invention the sensing device comprises a fourth amplifier connected to the detection coil arranged to amplify a detected signal of the detection coil.

In a further embodiment of the apparatus the first and second coils are provided with a channel to transport a cooling fluid. Cooling of the first and second coils also cools the detection coil and reducing a contribution of thermal noise in the detected signals. Cooling provides temperature stability of the apparatus at a substantially constant temperature.

The invention also relates to a sensing device for use in an apparatus according to any of the claims 6-14.

These and other aspects of the invention are apparent from and will be elucidated, by way of non-limitative example, with reference to the embodiments described hereinafter and the accompanying drawing.

Figure 1:
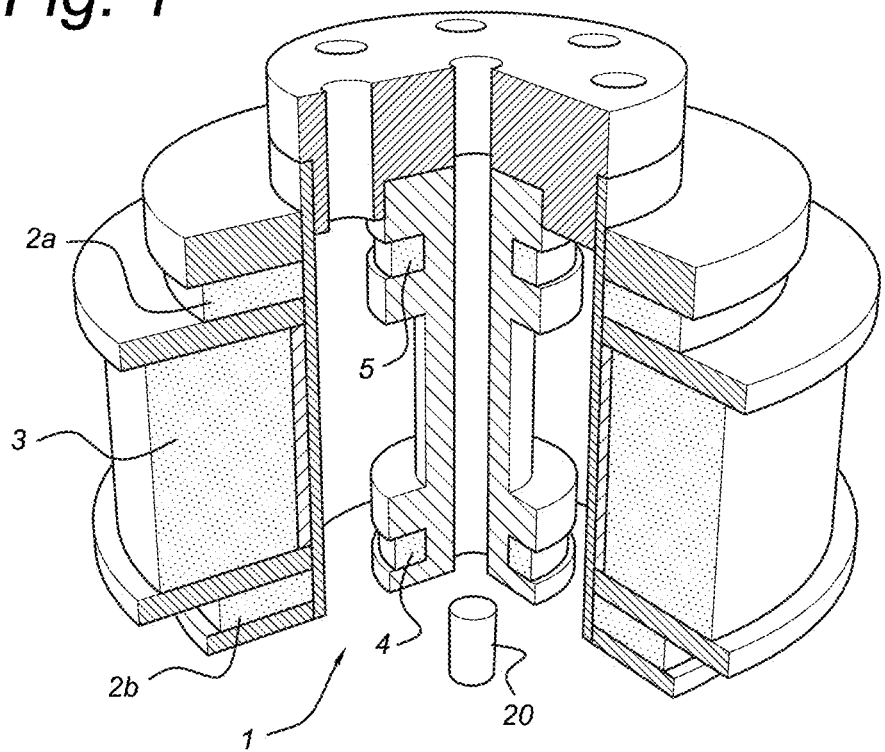
FIG. 1 shows an embodiment of the apparatus according to the invention.
Figure 2:
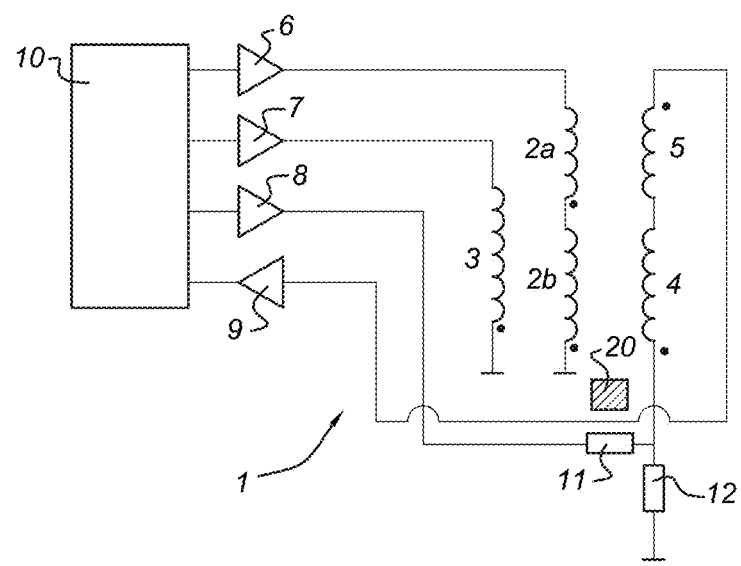
FIG. 2 shows schematically an electronic circuit of the apparatus according to the invention.

The apparatus or probe according to the invention is explained with respect to FIG. 1 and FIG. 2.

FIG. 1 shows an embodiment of the apparatus or probe 1 according to the invention for measuring an amount of superparamagnetic material in an object 20. FIG. 2 shows schematically an electronic circuit of the apparatus. The superparamagnetic material can comprise superparamagnetic iron oxide (SPION), for example, Endorem which can be obtained from Guerbet or Resovist which can be obtained from Bayer Schering Pharma AG. The apparatus can be used for the detection small amounts of SPIONs in an object 20. The object can be a sample or a body of a patient. For example, this SPION material can be introduced in a body of a patient and detected with the apparatus or probe 1. The detected position and quantity of the SPIONs can then be used in for example a Sentinel Lymph Node (SLN) procedure. The apparatus 1 comprises means 2a,2b and 3 arranged to apply a magnetic field comprising a first and a second component to the object. The means arranged to apply the magnetic field can comprise a first amplifier 6 and a first coil 2a,2b connected to the first amplifier for generating the first component of the magnetic field and a second amplifier 7 and a second coil 3, connected to the second amplifier 7. The second coil is arranged to generate the second component of the magnetic field.

The first amplifier 6 should be dimensioned for supplying a current of about 1.5 A at a amplitude of 1 V. In this embodiment the first coil 2a,2b is axially positioned with the second coil 3. Furthermore, the first coil 2 can consist of two identical sub coils 2a,2b, the first sub-coil 2a can be positioned at one side of the second coil 3 and the second sub-coil 2b can be positioned at the other side of the second coil 3.

The first coils 2a,2b and second coil 3 can be positioned in an axial setup in a frame. The frame can be made of Delrin. The radii of the first sub-coil and the second sub-coil can be 0.016 m. The length in axial direction can be for example 0.003 m. The inductance of the first and second sub-coil can be for example 36.6 µH.

The radius of the second coil is, for example, 0.025 m. The length in axial direction is 0.050 m. The inductance of the second coil is, for example, 2.22 mH. The first and second coils can be wound with Litze with a diameter of 1.24 mm. The apparatus 1 can further comprise a sensing device 4,5 for measuring a magnetization of the object 20.

Figure 3:
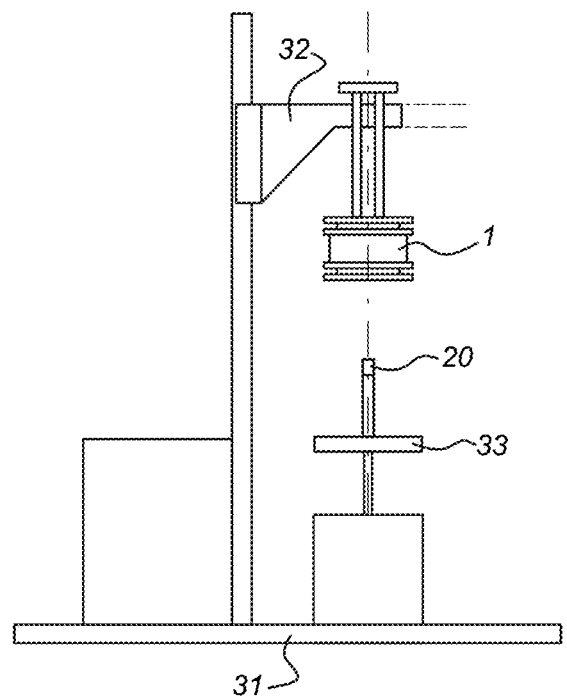
FIG. 3 shows an arrangement of a probe holder in which the apparatus of the invention can be used.

FIG. 3 shows an embodiment of the probe 1 and a probe holder. The embodiment further comprises a frame 31 and a probe holder 32 mounted on the frame 31. The frame further comprises a sample holder 33 for holder the object 20. The sample holder can also comprise a patient table, in which the first and second coils of the apparatus are integrated.

The sensing device 4,5 can comprise a detection coil 4 and a compensation coil 5. The detection coil and the compensation coil can be coaxially arranged with the first coil 2a,2b. In this embodiment the detection coil 4 is coaxially arranged with the first sub-coil 2b and the compensation coil 5 can be coaxially arranged with the second sub-coil 2a.

Furthermore, the compensation coil 5 is physically dimensioned and geometrically arranged to have a mutual inductance with the first coil 2a which is opposite to a mutual induction of the detection coil 4 with the first coil 2b.

The radii of the detection coil 4 and the compensation coil 5 are, for example, 0.008 m. The inductances of the detection coil 4 and the compensation coil 5 are, for example, 3.16 mH. The detection coil 4 and the compensation coil 5 can be wound with insulated copper wire with a diameter of 0.1 mm.

The apparatus further comprises a control device 10. The control device can be a personal computer provided with output ports comprising DA converters and an acquisition unit provided with an AD converter. The control device 10 is connected to the respectively the first and second amplifiers 6,7. The apparatus 1 further comprises a third amplifier 8, which is connected to a series circuit of the detection coil 4 and the compensation coil 5. The control device is connected to an input of the third amplifier 8. The control device 10 can be further arranged to provide a control signal to the third amplifier 8 to provide a compensation current to the detection coil 4 and the compensation coil 5. This compensation current generates a signal which is 180° out of phase with an induced potential difference $U_{ac}$ in the detection coil 4 and the compensation coil 5 due to a small difference in, respectively, the mutual inductance between the detection coil 4 and the first sub coil 2b and the mutual inductance between the compensation coil 5 and the first sub coil 2a. The output of the third amplifier 8 is connected to the series circuit of the detection coil 4 and the compensation coil 5 via a voltage divider consisting of the resistors 11,12.

The apparatus 1 further comprises a fourth amplifier 9, which can be arranged in the sensing device. An input of the fourth amplifier is connected to a series circuit between the detection coil 4 and the compensation coil. Between the input of the fourth amplifier 9 and the detection coil a low pass filer can be present to reject high frequency back ground signals. An output of the fourth amplifier 9 can be connected to an input of the control device 10. The input of the control device can be provided with an AD convertor (not shown). The fourth amplifier 9 is arranged to amplify a detected signal of the detection coil 4 and to transfer the amplified detected signal to the control device. The detected signal can be in the range between 0 and 10 μV and is amplified to match with an input range of the AD-converter at the input of the control device. In operation, the control device 10 is arranged to a) apply a magnetic field comprising a first component alternating with a first period to the object and having a magnetic field strength lower than a magnetic field strength at which the SPION is driven in saturation.
b) measuring a first magnetic susceptibility of the object with a detection coil 4;
c) applying a static second component to the magnetic field for a second period being equal or larger than the first period, the strength of the magnetic field during the second period is such that the SPION is driven towards saturation;
d) measuring a second magnetic susceptibility of the object with the detection coil during the application of the static second component; and e) determining the amount of SPION from a difference between the measured first and second values of the susceptibility of the object.

In this way differential susceptometry of the object can be performed.

The applied first alternating component of the magnetic field can be a sine wave having a single frequency and a first period in the range between, for example, 60 μs and 1 ms and is, for example, 0.1 ms. The magnetic field strength can be about 0.1 T, which is in a regime with the highest susceptibility of the SPIONs.

The object or sample 20 can be placed near the core of the first and second coils 2a,2b, 3 and near the detection coil 4. Alternatively, in case the object is a patient the patient can be positioned on a table 33 in which the first and second coils are integrated. The detection device 4 can be positioned near the parts of the body to be investigated. The magnetization response of the SPION introduces a changing flux in the detection coil and generates a detection signal. The detection signal is amplified by the fourth amplifier 9 and transferred to input of the control device 10.

The detected signal is proportional to the derivative of the magnetization response. The control device 10 is arranged to determine a first susceptibility $\chi_0$ from the detected signal In step c) a static second component to the magnetic field is applied. The second period in which this static second component is applied can be equal or larger than the first period. For example 10 ms. Furthermore, the strength of the magnetic field during the second period is such that the SPION is driven towards saturation.

Figure 4A:
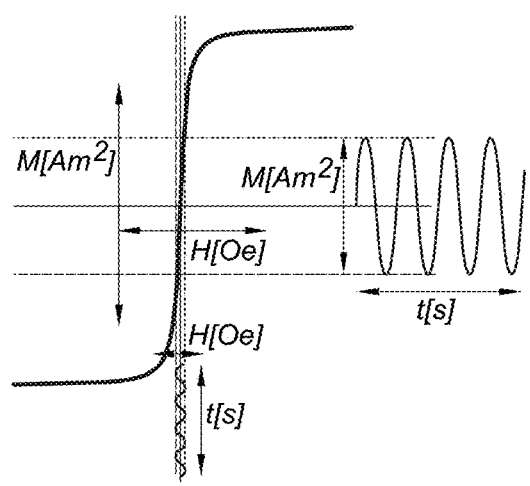
FIG. 4 shows the influence of an magnetic field with an alternating first component and a static second component on a superparamagnetic material and a paramagnetic material.
Figure 4B:
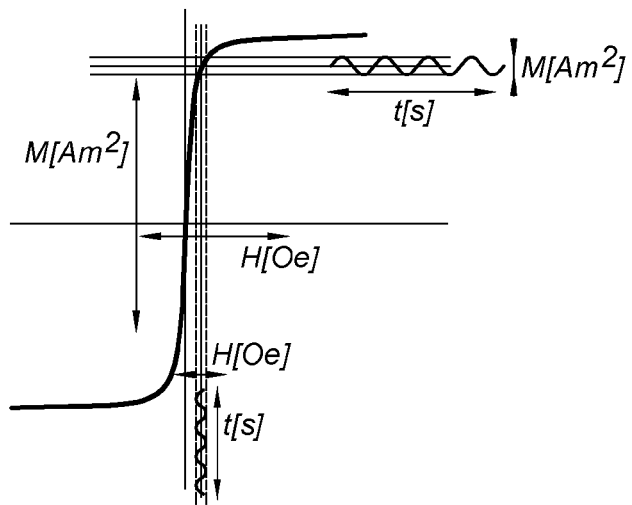
Figure 4C:
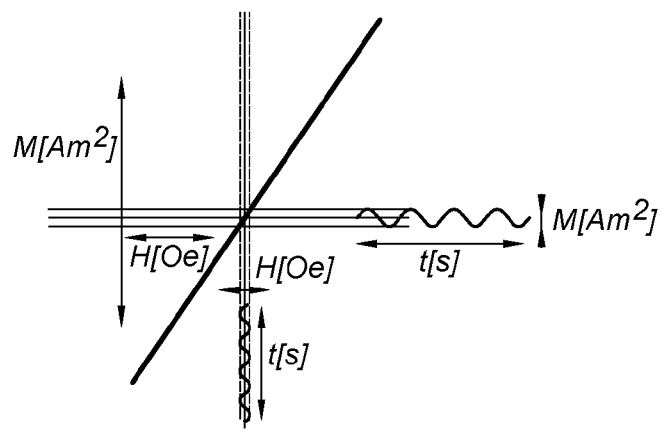
Figure 4D:
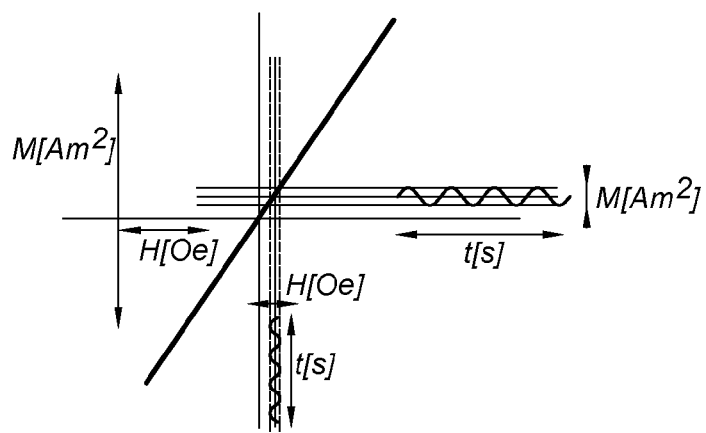

FIG. 4a shows the influence of an alternating magnetic field on the magnetization of SPION. The alternating magnetic field H creates an alternating magnetization M with a certain amplitude. FIG. 4b shows the influence of a static component or offset added to the alternating component. FIG. 4b shows that the amplitude of the alternating magnetization is smaller than that with respect to FIG. 4a. FIGS. 4c and 4d shows respectively the influence of an alternating magnetic field on the magnetization of a paramagnetic material and the influence of a static component added to the alternating magnetic field on a paramagnetic material. FIGS. 4c and 4d shows that the effect on the modulated magnetization is the same.

During the application of the static second component the induced voltage in the detection coils is again measured and then the control device determines a second susceptibility $\chi_1$.

The control device then determines a quantity of SPION in the sample from the difference between the values $\chi_1$ and $\chi_0$.

In an embodiment the control device is arranged to repeat the steps b) to d) with a third period, wherein the third period is equal to or larger than the second period, wherein in step c) a direction of the applied static component of the magnetic field in a further third period after a preceding second period can be reversed with respect to the direction of the applied second magnetic field in the preceding third period.

The second period is, for example, 50 ms, the third period is then, for example, 100 ms or the repeating frequency of the switching of the second component is 10 Hz.

The multiple measurement of first and second susceptibility $\chi_0$ and $\chi_1$ can be used to improve the accuracy of the detected quantities.

In this way it is possible to detect an amount of SPIONs in a range between 0.5 μg and 1000 μg.

Figure 5A:
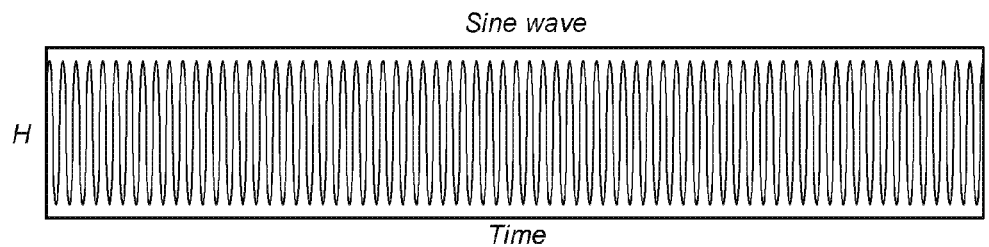
FIG. 5 shows timing diagrams of the first and second component of the applied magnetic field and the detected signal.
Figure 5B:
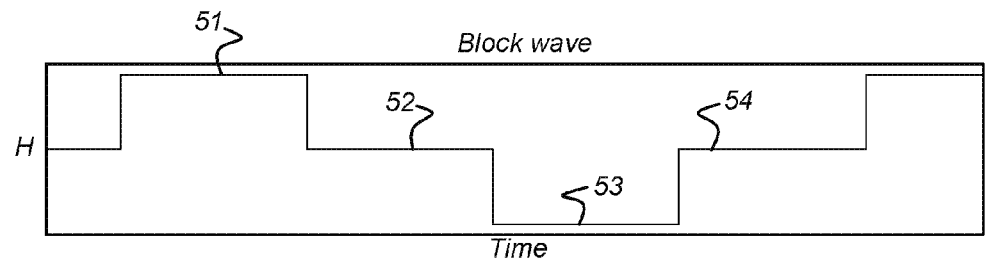
Figure 5C:
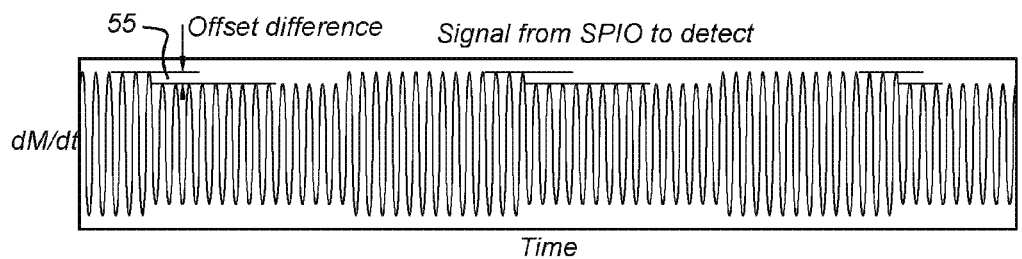

FIG. 5 shows a first diagram 5a representing a sine wave shaped current that can be applied to first coil 2a,2b for generating the first component of the magnetic field, a second diagram 5b representing a block wave shaped current that can be applied to the second coil 3 for generating the second component of the magnetic field and a third diagram 5c representing a detected signal from the detection coil 4. The block wave shaped current comprises two consecutive third periods. The first third period comprises a first portion 51 that is equal to the second period in which the static second component is added to the magnetic field and a second portion 52 in which the static second component is not applied. The second third period comprises a third portion 53 that is equal to the second period in which the static second component is applied to the magnetic field with a direction opposite to the direction of the static second component applied in the first portion, and a fourth portion 54 in which the static second component is not applied to the magnetic field.

Diagram 5c represents a detection signal showing a difference 55 in the amplitude modulation of the detected signal representing a modulation in the magnetization of the SPION due to the switching of the static second component of the magnetic field.

Although the invention is described using specific embodiments, it will be clear that multiple methods and arrangements are possible within the scope of the invention. The skilled person will be able to combine, adapt, change or leave out one or more of the disclosed specific features of the embodiments.

The invention claimed is:

1. Method for measuring an amount of superparamagnetic material in an object comprising:
   a) applying a magnetic field comprising a first component alternating with a first period and a single frequency to the object and having a magnetic field strength lower than a magnetic field strength at which the superparamagnetic material is driven into saturation;
   b) measuring a first magnetic susceptibility of the object with a detection coil;
   c) applying a static second component to the magnetic field for a second period being equal or larger than the first period, the strength of the magnetic field during the second period is such that the superparamagnetic material is driven towards saturation;
   d) measuring a second magnetic susceptibility of the object with the detection coil during the application of the static second component; and
   e) determining the amount of superparamagnetic material from a difference between the measured first and second susceptibility of the object,
   wherein the method comprises
   repeating steps b) to d) with a third period, wherein the third period is equal to or larger than the second period.

2. Method as claimed in claim 1, wherein in step c) a direction of the applied static component of the magnetic field in a further third period after a preceding second period is reversed with respect to the direction of the applied second magnetic field in the preceding third period.

3. Method as claimed in claim 1, wherein the superparamagnetic material comprises superparamagnetic iron oxide (SPIO).

4. Apparatus (1) for measuring an amount of superparamagnetic material in an object, comprising:
   at least two amplifiers and at least two coils (2a,2b, 3) arranged to apply a magnetic field comprising a first and a second component to the object (20);
   a sensing device (4) arranged to measure a magnetization of the object
   a control device (10) arranged to control the first component and second component of the magnetic field and the sensing device (4), wherein the control device (10) is arranged to perform the method according to claim 1.

5. Apparatus according to claim 4, wherein the apparatus comprises a first amplifier (6) and a first coil (2a,2b) connected to the first amplifier, the first coil is arranged to generate the first component of the magnetic field.

6. Apparatus according to claim 5, wherein the apparatus comprises a second amplifier (7) and a second coil (3), connected to the second amplifier, the second coil is arranged to generate the second component of the magnetic field.

7. Apparatus according to claim 5, wherein the sensing device comprises a detection coil (4).

8. Apparatus according to claim 7, wherein the sensing device further comprises a compensation coil (5) arranged to have a mutual inductance with the first coil which is opposite to a mutual induction of the detection coil (4) with the first coil.

9. Apparatus according to claim 8, wherein the compensation coil 5 is coaxially arranged within the first coil.

10. Apparatus according to claim 9, wherein the first coil comprises a first sub-coil (2a) and a second sub-coil (2b), wherein the first sub-coil (2a) is positioned with respect to one side of the second coil (3) and the second sub-coil (2b) is positioned with respect to the other side of the second coil (3).

11. Apparatus according to claim 10, wherein the first sub coil (2a) is coaxially arranged with the compensation coil (5) and the second sub coil (2b) is coaxially arranged with the detection coil (4).

12. Apparatus according to claim 4, wherein the sensing device (4) comprises a third amplifier (8) connected to a series circuit of the detection coil (4) and the compensation coil (5), wherein the control device is further arranged to control the third amplifier to provide a compensation current to the detection coil and the compensation coil.

13. Apparatus according to claim 5, wherein the sensing device comprises a fourth amplifier (9) connected to the detection coil arranged to amplify a detected signal of the detection coil (4).

14. A sensing device comprising a detection coil and for use in an apparatus according to claim 5.

15. Method as claimed in claim 2, wherein the superparamagnetic material comprises superparamagnetic iron oxide (SPIO).

16. Apparatus according to claim 6, wherein the sensing device comprises a detection coil (4).

17. Apparatus according to claim 6, wherein the first coil comprises a first sub-coil (2a) and a second sub-coil (2b), wherein the first sub-coil (2a) is positioned with respect to one side of the second coil (3) and the second sub-coil (2b) is positioned with respect to the other side of the second coil (3).

* * * * *